(12) United States Patent
Shalom et al.

(10) Patent No.: US 9,079,046 B2
(45) Date of Patent: Jul. 14, 2015

(54) FACIAL ANTIPERSPIRANT MOISTURIZING COMPOSITION AND METHOD OF PREPARING SAME

(76) Inventors: Zahava Shalom, Tel Aviv (IL); Meri Karako, Bat Yam (IL); Moshe Karako, Bat Yam (IL)

( * ) Notice: Subject to any disclaimer, the term of this patent is extended or adjusted under 35 U.S.C. 154(b) by 103 days.

(21) Appl. No.: 13/499,937

(22) PCT Filed: Oct. 14, 2010

(86) PCT No.: PCT/IL2010/000842
§ 371 (c)(1),
(2), (4) Date: Apr. 3, 2012

(87) PCT Pub. No.: WO2011/045794
PCT Pub. Date: Apr. 21, 2011

(65) Prior Publication Data
US 2012/0201771 A1  Aug. 9, 2012

(30) Foreign Application Priority Data

Oct. 15, 2009 (IL) .......................................... 201567

(51) Int. Cl.
| | |
|---|---|
| *A61Q 19/00* | (2006.01) |
| *A61K 8/04* | (2006.01) |
| *A61K 8/26* | (2006.01) |
| *A61K 8/89* | (2006.01) |
| *A61K 8/891* | (2006.01) |
| *A61K 8/894* | (2006.01) |
| *A61Q 15/00* | (2006.01) |

(52) U.S. Cl.
CPC ................ *A61Q 19/00* (2013.01); *A61K 8/042* (2013.01); *A61K 8/26* (2013.01); *A61K 8/891* (2013.01); *A61K 8/894* (2013.01); *A61Q 15/00* (2013.01)

(58) Field of Classification Search
CPC ........ A61K 8/042; A61K 8/26; A61Q 19/008
USPC .................................................... 424/401, 65
See application file for complete search history.

(56) References Cited

U.S. PATENT DOCUMENTS

| | | | |
|---|---|---|---|
| 4,120,948 | A | 10/1978 | Shelton |
| 6,007,799 | A | 12/1999 | Lee et al. |
| 6,110,473 | A | 8/2000 | Fitzpatrick et al. |
| 6,387,357 | B1* | 5/2002 | Chopra et al. ................... 424/65 |
| 7,431,918 | B2 | 10/2008 | Shelley et al. |
| 2005/0255075 | A1* | 11/2005 | Meder et al. ............. 424/70.122 |
| 2007/0048240 | A1* | 3/2007 | Slavashevich et al. .... 424/70.12 |
| 2008/0207737 | A1 | 8/2008 | Zinger |
| 2009/0130154 | A1 | 5/2009 | Gupta |
| 2009/0220444 | A1 | 9/2009 | Teckenbrock et al. |

FOREIGN PATENT DOCUMENTS

EP         1362581         11/2003

OTHER PUBLICATIONS

Notification Concerning Transmittal of International Preliminary Report on Patentability, dated Apr. 26, 2012 (7 pages).

* cited by examiner

*Primary Examiner* — Gina Justice
(74) *Attorney, Agent, or Firm* — Dicke, Billig & Czaja, PLLC

(57) ABSTRACT

The invention provides a cosmetic composition for reducing facial perspiration. The facial antiperspiration balm is a homogeneous mixture of a cosmetic gel and a cosmetic cream. The balm has a lowered amount of the active agent, moisturizes and protects the skin, and provides a pleasant feeling.

13 Claims, No Drawings

FACIAL ANTIPERSPIRANT MOISTURIZING COMPOSITION AND METHOD OF PREPARING SAME

FIELD OF THE INVENTION

The present invention relates to a cosmetic composition, and to a method of manufacturing same, for reducing facial perspiration. The facial antiperspiration balm is composed of homogeneously mixed cosmetic gel and cosmetic cream.

BACKGROUND OF THE INVENTION

Excessive perspiration is a response of sweat glands to thermal or emotional stimuli. As sweating may bring about a discomforting or embarrassing experience during occupational, sporting, or other social events, various treatments have been employed, including surgical removal of sweat glands or local administration of drugs affecting the nerve signals. The most common means include topically applying antiperspirants, mostly aluminum and zirconium salts, believed to obstruct the sweat gland ducts.

Localized control of sweating by topical means has long been a cosmetic goal, and although commercial antiperspirants were available already a hundred years ago, new challenges arise as more people exhibit irritation or allergic reactions, and as still stricter regulations are introduced into cosmetic practice, necessitating lower doses of active agents, allowing for lower antiperspirant effectiveness. Furthermore, some antiperspirant means may form stains on the clothes or on the skin. Various sites of the body may be affected by excessive sweating, sometimes called hyperhidrosis, but the most visible, and often the most undesirable, is the sweat formation on the lips, nose, forehead, face, scalp, and neck, which is called gustatory hyperhidrosis when associated with eating. To address facial sweating is a still more challenging task, in view of the sensitivity of this body part, and also in view of its visibility. It is therefore an object of this invention to provide a facial antiperspirant.

U.S. Pat. No. 4,120,948 describes an antiperspirant stick composed of two visible phases, comprising an annular gel shell and an anhydrous antiperspirant core of aluminum salt dispersed in waxy materials, the core containing 30-60 wt % of the active agent. U.S. Pat. No. 6,007,799 describes a clear cosmetic gel, aiming at increasing amounts of cosmetically active ingredients, comprising aluminum antiperspirant of up to 35 wt %. U.S. Pat. No. 6,110,473 describes a w/o/w emulsion with the aluminum active agent constituting more than 25 wt %. U.S. Pat. No. 7,431,918 provides anhydrous vehicle with calcium sulfate hemihydrate (plaster). US 2008/0207737 describes topical therapeutic compositions comprising anti-cholinergic or anti-muscarinic antagonists. The known compositions, and associated methods, have several drawbacks; some of the methods are too invasive; some of the compositions comprise too a high amount of active agents; some of the compositions do not deliver the active agent efficiently to the skin; some of the compositions leave visible deposits; some of the compositions have too a complex structure; some of the compositions would not be pleasant or gentle on the skin, for example, for lacking a suitable lipid component or suitable hydrophilic component. None of those compositions are suitable as a facial antiperspirant.

It is therefore another object of this invention to provide a facial antiperspirant avoiding the drawbacks of the prior art.

It is still another object of this invention to provide a moisturizing facial antiperspirant comprising a lowered amount of the active agent.

It is a further object of the invention to provide a facial antiperspirant which would efficiently reduce sweating, while providing a pleasant feeling on the skin.

It is a still further object of the invention to provide a facial antiperspirant which would efficiently reduce sweating, while protecting the skin.

Other objects and advantages of present invention will appear as description proceeds.

SUMMARY OF THE INVENTION

The present invention provides a facial antiperspirant moisturizing cosmetic composition, being a homogeneous mixture of a cosmetic gel and a cosmetic cream, wherein said gel comprises water, silicone, and an aluminum compound, and wherein said cream comprises an oil in water emulsion. When using the term "silicone" herein, liquid alkylated siloxanes are intended; the term "silicones", as used herein, comprises dimethylpolysiloxanes, dimethyloligosiloxanes, and dimethylcyclosiloxa-nes (the three preceding materials sometimes being called dimethicones), as well as dimethicone copolyols (suitable surfactants for preparing water/silicone emulsions; information on silicone products are available from Dow Corning); the term polysiloxanes is used herein interchangeably with the term silicone. Wherein the term "gel" is used herein, a homogeneous mixture of a hydrophilic phase and a silicone oil phase is intended, the hydrophilic phase comprising water and lower alcohols, such as ethanol or propylene glycol; preferably, said homogeneous mixture is, for example, water-in-silicone emulsion. The term "cosmetic gel" is intended to denote a gel as above defined, comprising only cosmetically acceptable components. The term "cosmetic cream", as used herein denotes a cosmetically acceptable oil-in-water emulsion, non-liquid at ambient temperature; namely, an internal oil phase is dispersed in external aqueous based phase, wherein said oil may comprise lipids or silicones or a mixture thereof, and wherein all components are cosmetically acceptable materials. The facial antiperspirant moisturizing cosmetic composition according to the invention preferably comprises an aluminum-zirconium salt, such as, for example, aluminum zirconium tetrachlorohydrex Gly. The salt is at least partially dissolved in an aqueous phase, which solution is, in one embodiment, dispersed in a silicone. In the facial antiperspirant moisturizing cosmetic composition according to the invention, said cosmetic gel constitutes preferably from 25 to 55 wt % of said composition, and more preferably from 35 to 45 wt % of said composition. A facial antiperspirant moisturizing cosmetic composition, according to one embodiment of the invention, is a homogeneous mixture of a cosmetic gel and a cosmetic cream, wherein said gel comprises water-in-silicone emulsion and an aluminum compound, and wherein said cream comprises an oil in water emulsion; said cosmetic gel comprises an aluminum-zirconium salt dissolved in an aqueous phase, which aqueous phase is preferably dispersed in one or more polysiloxanes. In another embodiment, a facial antiperspirant moisturizing cosmetic composition according to the invention comprises about 30 wt % lipids and polysiloxanes, and about 10 wt % alcohols selected from ethanol, propyleneglycol, and tripropylene glycol. The facial antiperspirant moisturizing cosmetic composition according to the invention preferably comprises from 4 to 18 wt % aluminum-zirconium salts, from 5 to 15 wt % polysiloxanes, from 5 to 30 wt % lipids, and from 5 to 15 wt % alcohols selected from ethanol, propylene glycol, and tripropylene glycol.

In the preferred facial antiperspirant moisturizing cosmetic composition according to the invention, said aluminum-zirconium compound constitutes from about 4 to about 15 wt % of said composition, which is less than usually present in antiperspirant composition.

The invention is directed to a method of manufacturing a facial antiperspirant moisturizing cosmetic composition, comprising combining at least two phases, resulting in a cosmetically acceptable mixture containing from about 4 to 18 wt % aluminum-zirconium salts, from about 5 to 15 wt % polysiloxanes, from about 5 to 30 wt % lipids, and from about 5 to 15 wt % alcohols selected from ethanol, propylene glycol, and tripropylene glycol. Said polysiloxanes may comprise linear dimethylpolysiloxcanes, cyclic dimethylsiloxanes, and dimethylpolysiloxane derivatized with polyoxyalkylene. In one embodiment of the invention, said method comprises i) admixing a water phase comprising alcohol(s) and an aluminum salt into a silicone phase, while intensively stirring, thereby providing a water-in-silicone emulsion cosmetic gel; ii) admixing an oil phase comprising at least two lipids, at least one of the lipids being a wax, into a water phase at a temperature higher than ambient temperature, while intensively stirring, thereby providing an oil-in-water emulsion cosmetic cream; iii) combining at ambient temperature 30-50 weight parts of said cosmetic gel obtained in step i) with 70-50 weight parts of said cosmetic cream obtained in step ii), and gently stirring, thereby to obtain a homogeneous mixture of cosmetic gel and cosmetic cream, for use as an antiperspirant; said cosmetic gel preferably comprises 10-25 wt % alcohols, 12-36 wt % aluminum salts, and 10-25 wt % alkylated polysiloxanes; said oil preferably comprises lipids and dimethylpolysiloxanes, and constitutes 10-65 wt % of said cream. In another embodiment of the invention, said method comprises combining at least three phases, a first phase comprising water and at least one alcohol selected from ethanol, propylene glycol, and tripropylene glycol, a second phase comprising lipids and polysiloxanes, and a third phase containing an aluminum-comprising salt; preferably said second phase is admixed into said first phase at higher than ambient temperature, followed by admixing said third phase, wherein the total concentration of said aluminum-comprising salt in said facial antiperspirant moisturizing cosmetic composition is lower than 15 wt %.

The antiperspirant moisturizing cosmetic composition of the invention may have a form of lotion, ointment, pomade, soft paste, and hard paste, and it may further comprise components adjusting its visual properties, olfactory properties, and consistency.

DETAILED DESCRIPTION OF THE INVENTION

It has now been found that combining a cosmetic cream with a cosmetic gel in one homogeneous mixture provides a superior carrier for aluminum salts in the preparation of facial cosmetic antiperspirant means. Particularly a cosmetically acceptable water/silicone based gel comprising an aluminum salt is advantageously combined with a cosmetically acceptable oil-in-water emulsion to provide an antiperspirant facial balm exhibiting a surprising combination of a good feel on the skin with a high sweat-reducing efficacy; the antiperspirant balm of the invention feels light and pleasant on the head skin while reducing facial perspiration at lower total amounts of aluminum salts in the composition. Said gel and cream may be prepared separately and mixed, or separate components of said gel and said cream may be combined as described.

The term "facial perspiration" is intended to describe the sweat formation on the lips, nose, forehead, face, scalp, and neck, regardless the physiological causes or the event circumstances of the sweating. It has been found that the balm of the invention reduces perspiration with the same efficacy as commercially obtained gels even at reduced amounts of aluminum salts totally applied on the skin, while the feel and touch of the balm on the skin is better. The balm is a stable homogeneous mixture of a cosmetic gel, such as for example a water-in-silicone emulsion gel comprising an aluminum salt, with a cosmetic cream. A skilled person will appreciate that said gel and said cream may be prepared in accordance with the procedures outlined herein, or by any procedures known in the art, followed by gentle mixing said gel and said cream to obtain a visually homogeneous composition. Stirring or agitation, more intensive than necessary for homogenizing the two components, is undesired, and may weaken or destroy the separation of microphases in the balm composition, leading to reduced stability of the product or its lowered cosmetic efficacy. For example, low force extrusion of the two parts and/or slow stirring may provide the required homogeneity, but any gentle means may be employed. Also possible, in accordance with the invention as described and exemplified, is combining separate components of gel and cream.

Any gel is suitable, which comprises a homogeneous mixture of an aqueous phase with silicones. A water/silicone emulsion may be involved, wherein an aluminum salt is preferably dissolved, at least partially, in an aqueous phase, which phase is dispersed in a silicone oil phase. An example of components to be used for making a suitable gel includes, without limitations, an aqueous phase comprising 10-25 wt % alcohols and 12-36 wt % aluminum salts; a silicones phase comprising approximately 10-30 wt % silicones, possibly volatile and non-volatile ones, including a silicone-based surface active agent; the wt % being percents of the whole gel weight. The gel may, for example, comprise from about 40 to about 80 wt % aqueous phase (water and alcohols), 15-30 wt % aluminum salts, and 10-25 wt % silicones. Said alcohols preferably comprise lower molecular weight alcohols, mono or polyhydric ones. The alcohols may, for example, comprise one or two or all of ethanol, propylene glycol, and tripropyleneglycol. The silicones comprise liquid dimethylpolysiloxanes and preferably at least one surfactant, such as a dimethicone copolyol, for example PEG/PPG-dimethicone. The silicones may, for example, comprise cyclic decamethyl cyclopentasiloxane, dimethylpolysiloxanes blocked with trimethylsiloxy units in an amount less than the cyclic one, and a dimethicone copolyol in an amount of, for example, 2-5 wt % of the total silicones. Silicones may comprise other alkyl or aryl siloxanes, such as, for example, phenyl trimethicone. The preferred aluminum salts comprise, without limitations, aluminum zirconium chlorohydrates. The gel may, for example, comprise aluminum zirconium tetrachlorohydrex Gly, in an amount of 16-24 wt % or less. The gel may comprise additional components, such as emollients, buffers, bulking agents, thickening agents, moisturizers, fragrance components, and preservatives.

For the balm of the invention, suitable is any cream which is a cosmetically acceptable oil-in-water emulsion, preferably any moisturizing cream. The cream may comprise, for example, 20-60 wt % oils, wherein the term "oil" herein includes lipids and silicones for the need of the emulsion definition. The term lipids, as used herein and in accordance with its usual meaning, is intended to include organic compounds oily to the touch, insoluble in water and soluble in nonpolar organic solvents, including fats, plant oils, waxes, and esters of fatty acids with other alcohols than glycerol and long fatty chain alcohols. The term wax, as used herein, is intended to include a type of lipid that contains long-chain alkanes, alcohols or carboxylic acids of said alkanes, and esters comprising said alcohols and acids, excluding esters with glycerin or other polyols. For example and without limitations, the cream may comprise, beside an aqueous phase, 50 wt % lipids and 5 wt % emulsifiers. The emulsifiers may, for example, comprise fatty acid esters of polyols. The cream usually comprises two or three types of waxes, and one or two esters of fatty acids and (lower) aliphatic alcohols, such as isopropyl palmitate or myristate. The oil in said oil-in-water emulsion may comprise silicone oils. The cream may comprise additional emollients, and also vitamins, buffers, bulking agents, thickening agents, moisturizers, fragrance components, and preservatives.

A facial antiperspirant moisturizing cosmetic composition according to the invention is constituted by the above gel and the above cream, gently homogenized in a weight ratio of from 1:3 to 3:2 of gel to cream, preferably about 2:3. A facial antiperspirant moisturizing cosmetic composition according to the invention is characterized by a lowered amount of metal salt than other available commercial antiperspirant means, which usually contain about 20 wt % of aluminum-zirconium salts. The instant facial antiperspirant composition typically contains less than 15 wt % aluminum zirconium salts. An antiperspirant balm according to the invention may contain, for example, 8 wt % aluminum zirconium tetrahydrex Gly, or 5 wt %. The composition is stable on storage, when not exposed to higher temperatures.

The method of manufacturing a facial antiperspirant moisturizing cosmetic composition according to the invention comprises i) providing components required for making a cosmetic gel, comprising water and silicone, ii) providing an aluminum salt; iii) providing components required for making a cosmetic cream comprising lipids and/or oils; and iv) mixing the components to provide the antiperspirant facial balm. The method may comprise i) providing a cosmetic gel, comprising aluminum and a water-in-silicone emulsion; ii) providing a cosmetic cream which is an oil-in-water emulsion; and iii) gently mixing at ambient or somewhat lower than ambient temperature said gel and cream, thereby obtaining a homogeneous composition to be used as an antiperspirant facial balm. Said step of providing the gel may comprise admixing a water phase comprising alcohol(s) and an aluminum salt into a silicone phase, while intensively stirring, and removing entrapped air bubbles, thereby providing a water-in-silicone emulsion cosmetic gel; and said step of providing the cream may comprise admixing an oil phase comprising at least two lipids, at least one of the lipids being a wax, and at least one emulsifier, into a water phase at a temperature higher than ambient temperature, for example at 60-90°, while intensively stirring, thereby providing an oil-in-water emulsion cosmetic cream. Said step of gently mixing the gel and the cream comprises combining 30-50 weight parts of said cosmetic gel with 70-50 weight parts of said cosmetic cream. In the above method, said cosmetic gel may comprise 10-25 wt % alcohols, 12-36 wt % aluminum salts, and about 10-35 wt %, alkylated polysiloxanes, while the oil in said cosmetic cream comprises lipids and dimethylpolysiloxanes, and constitutes 20-65 wt % of said cream, preferably 30-60 wt %.

The facial antiperspirant balm was tested on volunteers, who evaluated the feel on the skin, as well as the antiperspirant effect of the composition. The balm was favorably assessed by the most of the volunteers. The composition combines good spreadability and penetration of an oil-in-water cream with sustained moisturizing usually provided by a water-in-oil emulsion and with antiperspirant action of aluminum-containing gels, without usually observed tackiness of such gels.

Combining the two types of cosmetic preparations in one composition improves efficacy of the antiperspirant agent and also improves the feeling on the skin, particularly when the human subject is exposed to high temperature and humidity. The contribution of the gel to the composition may include i) increasing available moisture, and preventing dry skin sometimes observed when using the cream alone, ii) adjusting the texture and spreadability of the composition, and iii) causing a slight pleasant tension in the skin (gel alone brings about such tension too aggressively), further also rendering to the skin an appearance of gleam and freshness. The contribution of the cream to the composition may include i) tuning the skin tension caused by the gel, ii) creating the light feeling, and reducing eventual greasy and sticky feelings caused by gels when used alone, iii) adjusting good skin spreadability and penetration, iv) adding an active hydration effect by the external water phase of the cream emulsion, and v) protecting the skin by providing oils onto its surface. The antiperspirant balm of the invention, thus, provides the efficient antiperspirant effects, and simultaneously provides protecting and hydrating effects. Importantly, the combination of the components and phases seems to provide an efficient means for delivering the active agent, namely the metal antiperspirant salts, to its target site in the skin. Without wishing to be limited by any theory, it may be that the special multiphase microstructure of the composition of the invention enables to better deliver the metal cations into the sweat gland ducts where they form insoluble complexes obstructing the ducts, without the need of excessively high salt concentrations of the known antiperspirant compositions. The balm of the invention should reduce sweating at time periods when the reasons for sweating appear, and it should protect and moisturize the skin in the periods when the reasons disappear.

When tested on volunteers, the facial antiperspirant moisturizing cosmetic composition of the invention reduced or stopped sweating for a period of several hours or more, depending on the concentration of aluminum salt. The cosmetic composition also smoothened and strengthened the facial skin. It caused a pleasant feeling on the skin, supported also by the low pH. It provided and kept moisture in the dermis. The composition kept the skin elastic for prolonged periods, caused pleasant tension on the skin, and reduced the wrinkles. It rendered the skin smooth and pleasant to touch.

The invention will be further described and illustrated in the following example.

EXAMPLE

Example 1

A gel, similar to commercially available antiperspirant sticks, was provided, comprising less than 25 wt % alcohols (ethanol, propylene glycol, and tripropylene glycol in approximately equal amounts), less than 25 wt % alkylated polysiloxanes (cyclopentasiloxane, dimethylpolysiloxane, phenyl trimethicone, PEG/PPG-18/18 dimethicone), about 18 wt % aluminum zirconium tetrachlorohydrex Gly, and fragrances, the rest being water. A cosmetic cream was provided, similar to commercially available face creams, comprising about 50 wt % waxes (microcrystalline wax, ozokerite wax, carnauba wax) and silicones (cyclopentasiloxane, dimethicone), 5 wt % emulsifiers and fatty esters, buffer, and fragrances, the rest being water. Four weight parts of the above gel and six weight parts of the above cream were mixed and pushed through a fine plastic net, and slowly stirred till obtaining a homogeneous composition.

The above composition was given to 112 volunteers to be put on the face daily during seven days. The volunteers were not informed about the composition constituents or the purpose of the test, and they were given question-forms to be filled at the end of the test. The question-form queried the users' opinion about i) the composition, including texture, aroma, touch, and ease in applying; ii) the feeling when applying the cream onto the skin, including the presence of tension, and irritation; and iii) the feeling after an exposure to the sun or after physical exercise, including the level of eventual irritation, itching, and face sweating. The answers showed that the composition according to the invention reduced sweating and gave a good feeling on the skin nearly to a majority of the volunteers.

Example 2

The following parts were prepared (the quantities are in wt %, trade names are in the brackets):
Phase No. 1:

| | |
|---|---|
| soft water | 54.0 |
| propylene glycol | 5.00 |
| EDTA tetrasodium | 0.10 |
| *Aloe Vera* powder | 0.10 |
| hydroxyethyl cellulose (Natrosol 250) | 0.05 |
| allantoin | 0.15 |
| methyl paraben | 0.15 |

Phase No. 2:

| | |
|---|---|
| C12-15alkyl benzoate (Finsolv TN) | 6.00 |
| C8/C10 caprylic/capric triglyceride (myritol 318) | 2.00 |
| dimethicone 350 (DC silicone 350) | 3.00 |
| phenyl dimethicone (DC silicone 593) | 0.50 |
| glycerol monostearate (Faci GMS-40AP) | 3.00 |
| cetyl alcohol (Thaiol1698) | 3.00 |
| PEG40-stearate (TEgacid S40P or Myrj 52) | 1.10 |
| sorbitan tristearate (Emulgade S65 or Span 65) | 0.28 |
| glyceryl monostearate & PEG-100 stearate (Emulgade 165 or Arlacer 165) | 1.00 |
| tocopherylacetate (vitamin E acetate) | 0.10 |
| butylhydroxytoluene (BHT) | 0.05 |
| propylparaben | 0.15 |
| cyclpentasiloxane (Cyclomethicone 245 or Belsil 040 or BC5) | 10.0 |

Phase No. 3:

| | |
|---|---|
| aluminumZirconium GLY, tetrachlorhydrex (Rezal 36P, powder) | 5.00 |

Phase No. 4

| | |
|---|---|
| ethanol 95% (denaturated alcohol 95%) | 5.00 |
| fragrance | 0.25 |

Phase No. 5

| | |
|---|---|
| DC yellow no. 5 1% solution | 0.06 |
| DC red no. 4 1% solution | 0.06 |

Phase no. 1 was prepared by mixing water and propylene glycol, at room temperature, 1000-1500 rpm, Marine or Anchor type, followed by adding powder ingredients, and then heating to 75° C. Phase no. 2 was prepared in a separate vessel by mixing all ingredients except for cyclopentasiloxane, heating at 70° C. to melt completely the solid ingredients, followed by adding cyclopentasiloxane and continuing mixing for 5 minutes. Phase 2 was poured into Phase 1 and homogenized by a high-speed homogenizer (such as Silverston or IKA types) for 10 minutes; mixing was continued by the Marine or Anchor at is 70° C., and then Phase 3 was added during 5-10 minutes; the mixture was cooled to 40° C., and Phases 4 and 5 were added. The specifications comprised: color according to the standard; pH 3.0-3.5; viscosity, Brookfieald LT, SPINDLE 3, SPEED 03, 60.000-75.000 CPS, RT.

While this invention has been described in terms of some specific examples, many modifications and variations are possible. It is therefore understood that within the scope of the appended claims, the invention may be realized otherwise than as specifically described.

The invention claimed is:

1. A facial antiperspirant moisturizing cosmetic balm composition, being a homogeneous mixture of two microphases, one being a cosmetic gel and a the other being cosmetic cream, wherein said gel constitutes from 25 to 55 wt % of said composition and comprises a water-in-silicone emulsion and an aluminum compound, and wherein said cream comprises an oil-in-water emulsion, the oil comprising waxes, and wherein the two microphases are separated in the balm composition.

2. A facial antiperspirant moisturizing cosmetic composition according to claim 1, wherein said cosmetic gel comprises an aluminum-zirconium salt dissolved in an aqueous phase, which aqueous phase is dispersed in one or more polysiloxanes.

3. A facial antiperspirant moisturizing cosmetic composition according to claim 1, wherein said mixture comprises about 30 wt % lipids and polysiloxanes, and about 10 wt % alcohols selected from ethanol, propylene glycol, and tripropylene glycol .

4. A facial antiperspirant moisturizing cosmetic composition according to claim 1, wherein said cosmetic gel constitutes from 35 to 45 wt % of said composition.

5. A facial antiperspirant moisturizing cosmetic composition according to claim 1, comprising from 4 to 18 wt % aluminum-zirconium salts, from 5 to 15 wt % polysiloxanes, from 5 to 30 wt % lipids, and from 5 to 15 wt % alcohols selected from ethanol, propylene glycol, and tripropylene glycol.

6. A facial antiperspirant moisturizing cosmetic composition according to claim 1, comprising from 5 to 15 wt % polysiloxanes, from 5 to 30 wt % lipids, and from 5 to 15 wt % alcohols selected from ethanol, propylene glycol, and tripropylene glycol, and further an aluminum-zirconium compound in an amount of from about 5 to about 10 wt % of said composition.

7. A method of manufacturing the facial antiperspirant moisturizing cosmetic composition of claim 1, comprising combining at least two phases, a first phase comprising a cosmetic gel and a second phase comprising a cosmetic cream, wherein said gel comprises water-in-silicone emulsion and an aluminum compound, and wherein said cream comprises an oil-in-water emulsion, resulting in a cosmetically acceptable homogeneous mixture containing from about 4 to 18 wt % aluminum-zirconium salts, from about 5 to 15 wt % polysiloxanes, from about 5 to 30 wt % lipids, and from about 5 to 15 wt % alcohols selected from ethanol, propylene glycol, and tripropylene glycol.

8. A method according to claim 7, comprising
   i) admixing a water phase comprising said alcohols and an aluminum salt into a silicone phase, while intensively stirring, thereby providing a water-in-silicone emulsion cosmetic gel;
   ii) admixing an oil phase comprising at least two lipids, at least one of the lipids being a wax, into a water phase at a temperature higher than ambient temperature, while intensively stirring, thereby providing an oil-in-water emulsion cosmetic cream;

iii) combining at ambient temperature 30-50 weight parts of said cosmetic gel obtained in step i) with 70-50 weight parts of said cosmetic cream obtained in step ii), and gently stirring, thereby to obtain a homogeneous mixture of cosmetic gel and cosmetic cream, for use as an antiperspirant.

9. A method according to claim 8, wherein said cosmetic gel comprises 10-25wt % alcohols, 12-36 wt % aluminum salts, and 10-25 wt % alkylated polysiloxanes.

10. A method according to claim 8, wherein said oil phase further comprises dimethylpolysiloxanes, and constitutes 10-65 wt % of said cream.

11. A method according to claim 7, wherein said polysiloxanes are selected from the group consisting of linear dimethylpolysiloxanes, cyclic dimethylsiloxanes, and dimethylpolysiloxane derivatized with polyoxyalkylene.

12. A method according to claim 7, comprising combining at least three phases, the first phase comprising water and at least one alcohol selected from ethanol, propylene glycol, and tripropylene glycol, the second phase comprising lipids and polysiloxanes, and the third phase containing an aluminum-comprising salt.

13. A method according to claim 12, comprising admixing said second phase into said first phase at higher than ambient temperature, followed by admixing said third phase, wherein the total concentration of said aluminum-comprising salt in said facial antiperspirant moisturizing cosmetic composition is lower than 15 wt %.

\* \* \* \* \*